United States Patent
Soykal et al.

(10) Patent No.: US 11,684,906 B2
(45) Date of Patent: Jun. 27, 2023

(54) OLEFIN ISOMERIZATION CATALYSTS

(71) Applicant: BASF Corporation, Florham Park, NJ (US)

(72) Inventors: Ibrahim Ilgaz Soykal, Beachwood, OH (US); Burcu Bayram, Iselin, NJ (US); Knut Wassermann, Union, NJ (US); Joseph C. Dellamorte, Beachwood, OH (US)

(73) Assignee: BASF CORPORATION, Florham Park, NJ (US)

( * ) Notice: Subject to any disclaimer, the term of this patent is extended or adjusted under 35 U.S.C. 154(b) by 0 days.

(21) Appl. No.: 16/972,867

(22) PCT Filed: May 30, 2019

(86) PCT No.: PCT/US2019/034627
§ 371 (c)(1),
(2) Date: Dec. 7, 2020

(87) PCT Pub. No.: WO2019/240958
PCT Pub. Date: Dec. 19, 2019

(65) Prior Publication Data
US 2021/0245138 A1    Aug. 12, 2021

Related U.S. Application Data

(60) Provisional application No. 62/684,874, filed on Jun. 14, 2018.

(51) Int. Cl.
| | | |
|---|---|---|
| *B01J 21/10* | (2006.01) | |
| *B01J 35/10* | (2006.01) | |
| *B01J 35/02* | (2006.01) | |
| *B01J 35/00* | (2006.01) | |
| *B01J 37/08* | (2006.01) | |
| *C07C 6/04* | (2006.01) | |
| *C07C 5/25* | (2006.01) | |
| *B28B 3/20* | (2006.01) | |

(52) U.S. Cl.
CPC ............. *B01J 21/10* (2013.01); *B01J 35/002* (2013.01); *B01J 35/026* (2013.01); *B01J 35/1014* (2013.01); *B01J 35/1019* (2013.01); *B01J 35/1038* (2013.01); *B01J 35/1042* (2013.01); *B01J 37/082* (2013.01); *C07C 5/2512* (2013.01); *C07C 6/04* (2013.01); *B28B 3/20* (2013.01); *C07C 2521/04* (2013.01); *C07C 2521/10* (2013.01); *C07C 2523/02* (2013.01)

(58) Field of Classification Search
CPC . B01J 21/04; B01J 21/10; B01J 35/002; B01J 35/026; B01J 37/82
See application file for complete search history.

(56) References Cited

U.S. PATENT DOCUMENTS

| | | | | |
|---|---|---|---|---|
| 3,533,963 | A | * | 10/1970 | Gignier ................ B01J 23/866 502/328 |
| 3,931,053 | A | * | 1/1976 | Kazakov ................ C01B 3/40 502/328 |
| 5,603,983 | A | | 2/1997 | Clough et al. |
| 7,977,522 | B2 | | 7/2011 | Takai et al. |
| 8,440,874 | B2 | | 5/2013 | Ramachandran et al. |
| 9,700,874 | B2 | * | 7/2017 | Bartek ................ C10G 1/06 |

FOREIGN PATENT DOCUMENTS

| | | |
|---|---|---|
| CA | 2598501 A1 | 9/2006 |
| EP | 1854776 A1 | 11/2007 |
| WO | 91/13882 A1 | 9/1991 |

OTHER PUBLICATIONS

International Search Report for PCT/US19/34627 dated Aug. 26, 2019, 8 pages.
Mierczynski Pawel et al., "Biodiesel Production on MgO, CaO, SrO and BaO Oxides Supported on (SrO)(Al2O3) Mixed Oxide", Catalysis Letters, vol. 145, No. 5, Mar. 3, 2015, pp. 1196-1205.

* cited by examiner

*Primary Examiner* — Yong L Chu
(74) *Attorney, Agent, or Firm* — Lowenstein Sandler LLP

(57) ABSTRACT

A catalyst composition comprising MgO, $Al_2O_3$ and one or more further alkaline earth metal oxides, provides for outstanding catalytic production of propylene when employed together with a metathesis catalyst.

15 Claims, No Drawings

OLEFIN ISOMERIZATION CATALYSTS

CROSS-REFERENCE TO RELATED APPLICATION(S)

This application is a national phase of International Application No. PCT/US2019/034627, filed on May 30, 2019, which claims the benefit of U.S. Provisional Patent Application No. 62/684,874, filed on Jun. 14, 2018. The contents of these applications are hereby incorporated by reference in their entirety.

FIELD OF THE INVENTION

The invention is directed towards olefin isomerization catalysts. In some embodiments, the catalysts comprise magnesia, alumina and one or more further alkaline earth metal oxides.

BACKGROUND

Propylene is an important chemical building block, employed for example to produce polypropylene, methyl acrylate, propylene oxide, cumene, oxo alcohols, isopropyl alcohol, acetone, etc. Propylene may be produced as a by-product of steam cracking or catalytic cracking. Increased demand for propylene has given rise to the need for "on-purpose" propylene production. On-purpose propylene production methods include a metathesis reaction of 2-butene with ethylene in the presence of a metathesis catalyst. 2-butene may be prepared via isomerization of 1-butene in the presence of an olefin isomerization catalyst.

The metathesis reaction employs a catalyst such as silica supported tungsten oxide. Tablet forms of MgO are generally employed as a co-catalyst in an overall olefin isomerization-metathesis process of producing propylene from 1-butene. Desired are olefin isomerization catalysts having improved performance.

SUMMARY

Accordingly, disclosed is a catalyst composition comprising MgO, $Al_2O_3$ and one or more further alkaline earth metal oxides. In some embodiments, the catalyst composition is in a shaped form.

Also disclosed is a method to prepare a catalyst composition, the method comprising preparing a mixture comprising i) MgO and/or $Mg(OH)_2$, ii) alumina and iii) oxides and/or hydroxides of one or more further alkaline earth metals; shaping the mixture into a shaped form;
drying the shaped form; and calcining the dried, shaped form.

Also disclosed is a method of preparing propylene, the method comprising contacting a feed stream containing 1-butene with ethylene in the presence of a catalyst composition comprising MgO, $Al_2O_3$ and one or more further alkaline earth metal oxides and a metathesis catalyst.

Also disclosed is a method of isomerizing 1-butene to 2-butene, the method comprising contacting a feed stream containing 1-butene with a catalyst composition comprising MgO, $Al_2O_3$ and one or more further alkaline earth metal oxides.

DETAILED DISCLOSURE

The present catalyst compositions comprise MgO, $Al_2O_3$ and one or more further alkaline earth metal oxides, "further" meaning further to MgO. Further alkaline earth metal oxides include CaO, SrO and BaO. In certain embodiments, the further alkaline earth metal oxide is CaO.

It has been found that the present catalyst compositions have improved crush strength. In some embodiments, the catalyst composition exhibits a crush strength of ≥2.0 lbs/mm (pounds per millimeter), ≥2.2 lbs/mm, ≥2.4 lbs/mm, ≥2.6 lbs/mm, ≥2.8 lbs/mm, ≥3.0 lbs/mm, ≥3.2 lbs/mm, ≥3.4 lbs/mm, ≥3.6 lbs/mm, ≥3.8 lbs/mm or ≥4.0 lbs/mm.

The term "crush strength" refers to single piece crush strength or piece crush strength. Crush strength may be defined as the resistance of a formed catalyst to compressive forces. Measurements of crush strength are intended to provide indication of the ability of a catalyst to maintain its physical integrity during handling and use. Piece crush strength may be measured by placing an individual catalyst, whether in the form of an extrudate, tablet or otherwise, between two flat surfaces and applying a compressive load to the catalyst or through the two flat surfaces to the catalyst and measuring the force required to crush the piece. The flat surfaces may be dies having area width of about 0.125 in (3 mm). The force required to crush the piece between the flat surfaces may be measured by a force transducer. Crush strength may be determined according to ASTM D4179-11.

Present catalyst compositions when in use may be in a "shaped form", for example in a shaped form selected from a group consisting of agglomerates, tablets, rings, stars, wagon wheels, extrudates, rods, spheres, spheroids, cylinders, briquettes and pellets. The catalyst compositions having improved crush strength allows for formation of high surface area extrudates which can withstand the pressure of hydrocarbon flow and stress in a reactor.

Extrudates in some embodiments include cylinder-like shaped forms. Cylinder-like shaped forms include cylinders, trilobes, quadralobes, star shapes and hollow cylinders. In other embodiments, extrudates include star-like shaped forms.

Star-like shapes may include 3, 4, 5, 6, 7, or 8 pointed star shapes. In some embodiments, a star shape may have a longest distance between any two points of from any of about 1 mm, about 2 mm, about 3 mm or about 4 mm to any of about 5 mm, about 6 mm, about 7 mm or about 8 mm; and may have an average length of from any of about 2 mm, about 3 mm, about 4 mm, about 5 mm, about 6 mm, about 7 mm or about 8 mm to any of about 9 mm, about 10 mm, about 12 mm, about 14 mm, about 16 mm, about 18 mm or about 20 mm.

In some embodiments, the shaped forms are prepared by a process comprising preparing a mixture comprising i) MgO and/or $Mg(OH)_2$, ii) alumina and iii) oxides and/or hydroxides of one or more further alkaline earth metals; shaping the mixture into a shaped form; drying the shaped form; and calcining the dried, shaped form.

In some embodiments, shaping includes tableting, extrusion or pressing. In some embodiments, drying is performed at a temperature and for a time sufficient to remove substantially all water and/or other volatiles. In some embodiments, drying may be performed prior to the shaping step. Drying may be performed for example from any of about 50° C., about 60° C., about 70° C. or about 80° C. to any of about 90° C., about 100° C., about 110° C., about 120° C. or about 130° C. for a time of from any of about 1 h (hour), about 2 h, about 4 h, about 6 h or about 8 h to any of about 10 h, about 12 h, about 15 h, about 18 h, about 21 h or about 24 h. Calcination may be performed at a temperature of from any of about 300° C., about 325° C., about 350° C., about 375° C., about 400° C. or about 425° C. to any of about 450°

C., about 475° C., about 500° C., about 525° C., about 550° C., about 575° C. or about 600° C. for a time of from any of about 0.5 h, about 1.0 h, about 1.5 h, about 2.0 h or about 2.5 h to any of about 3.0 h, about 3.5 h, about 4.0 h, about 4.5 h, about 5.0 h or about 5.5 h.

In some embodiments, the shaped form may have an average largest diameter from any of about 1 mm, about 2 mm, about 3 mm, about 4 mm, about 5 mm, about 6 mm, about 7 mm, about 8 mm, about 9 mm or about 10 mm to any of about 12 mm, about 14 mm, about 16 mm, about 18 mm, about 20 mm, about 22 mm, about 24 mm or about 25 mm. Largest diameter refers to the largest measurement of any form.

In some embodiments, the catalyst composition is in a cylinder-like shaped form. A cylinder-like shaped form will have an average diameter and an average length. In some embodiments, a cylinder-like shaped form may have an average diameter of from any of about 1 mm, about 2 mm, about 3 mm or about 4 mm to any of about 5 mm, about 6 mm, about 7 mm or about 8 mm; and may have an average length of from any of about 2 mm, about 3 mm, about 4 mm, about 5 mm, about 6 mm, about 7 mm or about 8 mm to any of about 9 mm, about 10 mm, about 12 mm, about 14 mm, about 16 mm, about 18 mm or about 20 mm. In some embodiments, a cylinder-like shaped form will have an average length that is greater than or equal to an average diameter. In other embodiments, a cylinder-like shaped form may have an average length that is less than or equal to an average diameter.

In certain embodiments, the catalyst composition may also comprise one or more of $Mg(OH)_2$, $Al(OH)_3$, or hydroxides of one or more further alkaline earth metals. In some embodiments, the catalyst composition may comprise from any of about 0.1 wt %, about 0.2 wt %, about 0.5 wt %, about 1 wt %, about 2 wt %, about 3 wt %, about 4 wt %, about 5 wt %, about 6 wt %, about 7 wt %, about 8 wt %, about 9 wt % or about 10 wt % to any of about 11 wt %, about 12 wt %, about 15 wt %, about 20 wt %, about 25 wt %, about 30 wt %, about 35 wt % or about 40 wt %, of one or more of $Mg(OH)_2$, $Al(OH)_3$, or hydroxides of one or more further alkaline earth metals, in total, based on the total weight of the composition.

In some embodiments, the catalyst composition may comprise from any of about 25 wt % (weight percent), about 30 wt %, about 35 wt %, about 40 wt % or about 45 wt % to any of about 50 wt %, about 55 wt %, about 60 wt %, about 65 wt %, about 70 wt % or about 75 wt % MgO, based on the total weight of the composition.

In some embodiments, the catalyst composition may comprise from any of about 20 wt %, about 25 wt %, about 30 wt % or about 40 wt % to any of about 45 wt %, about 50 wt %, about 55 wt % or about 60 wt % $Al_2O_3$, based on the total weight of the composition.

In some embodiments, the catalyst composition may comprise from any of about 3 wt %, about 4 wt %, about 5 wt %, about 6 wt %, about 7 wt %, about 8 wt %, about 9 wt % or about 10 wt % to any of about 11 wt %, about 12 wt %, about 13 wt %, about 14 wt %, about 15 wt %, about 16 wt %, about 17 wt %, about 18 wt %, about 19 wt % or about 20 wt % of the one or more further alkaline earth metal oxides, in total, based on the total weight of the composition.

In some embodiments, the catalyst composition may comprise MgO to $Al_2O_3$ in a weight/weight ratio (MgO/$Al_2O_3$) from any of about 1/9, about 1/8, about 1/7, about 1/6, about 1/5, about 1/4, about 1/3, about 1/2 or about 1/1 to any of about 2/1, about 3/1, about 4/1, about 5/1, about 6/1, about 7/1, about 8/1 or about 9/1. In some embodiments, the catalyst composition may comprise a weight/weight ratio of MgO/$Al_2O_3$ from any of about 0.50/1.00, about 0.75/1.00, about 1.00/1.00 or about 1.25/1.00 to any of about 1.50/1.00, about 1.75/1.00, about 2.00/1.00 or about 2.25/1.00.

In some embodiments, the catalyst composition may comprise MgO to the one or more further alkaline earth metal oxides, in total, in a weight/weight ratio (MgO/one or more further alkaline earth metal oxides, in total) from any of about 20/1, about 18/1, about 16/1, about 14/1, about 12/1, about 10/1, about 8/1, about 6/1 or about 5/1 to any of about 4/1, about 3/1, about 2/1 or about 1/1. In some embodiments, the catalyst composition may comprise a weight/weight ratio of MgO/one or more further alkaline earth metal oxides, in total, from any of about 6.50/1.00, about 6.25/1.00, about 6.00/1.00, about 5.75/1.00, about 5.50/1.00, about 5.25/1/00 or about 5.00/1.00 to any of about 4.75/1.00, about 4.50/1.00, about 4.25/1.00, about 4.00/1.00, about 3.75/1.00 or about 3.50/1.00.

In certain embodiments, the catalyst composition comprises from any of about 40 wt %, about 41 wt %, about 42 wt %, about 43 wt %, about 44 wt %, about 45 wt %, about 46 wt %, about 47 wt % or about 48 wt % to any of about 49 wt %, about 50 wt %, about 51 wt %, about 52 wt %, about 53 wt %, about 54 wt %, about 55 wt %, about 56 wt %, about 57 wt %, about 58 wt %, about 59 wt % or about 60 wt % MgO, based on the total weight of the composition. In some embodiments, the catalyst composition comprises from about 35 wt %, about 36 wt %, about 37 wt %, about 38 wt %, about 39 wt % or about 40 wt % to any of about 41 wt %, about 42 wt %, about 43 wt %, about 44 wt %, about 45 wt %, about 46 wt %, about 47 wt %, about 48 wt %, about 49 wt % or about 50 wt % $Al_2O_3$, based on the total weight of the composition. In some embodiments, the catalyst composition comprises from any of about 5 wt %, about 6 wt %, about 7 wt %, about 8 wt % or about 9 wt % to any of about 10 wt %, about 11 wt %, about 12 wt %, about 13 wt %, about 14 wt % or about 15 wt % of the one or more further alkali metal oxides, in total, based on the total weight of the catalyst composition.

In certain embodiments, the catalyst composition comprises about 49 wt %, about 50 wt % or about 51 wt % MgO, about 39 wt %, about 40 wt % or about 41 wt % $Al_2O_3$ and about 9 wt %, about 10 wt % or about 11 wt % of one or more of CaO, SrO or BaO, in total, based on the total weight of the catalyst composition.

Present catalyst compositions may have a pore volume of from any of about 0.30 $cm^3/g$, about 0.33 $cm^3/g$, about 0.36 $cm^3/g$, about 0.39 $cm^3/g$ or about 0.42 $cm^3/g$ to any of about 0.45 $cm^3/g$, about 0.48 $cm^3/g$, about 0.51 $cm^3/g$, about 0.54 $cm^3/g$, about 0.57 $cm^3/g$, about 0.60 $cm^3/g$, about 0.63 $cm^3/g$, about 0.66 $cm^3/g$, about 0.69 $cm^3/g$ or about 0.72 $cm^3/g$.

Pore volume may be measured by mercury intrusion porosimetry, for example according to ASTM D4284. In another embodiment, the pore volume may be determined by nitrogen physisorption.

The catalyst compositions may have an average pore size, reported as pore radius, from any of about 3 nm (nanometers), about 4 nm, about 5 nm, about 6 nm, about 7 nm, about 8 nm, about 9 nm or about 10 nm to any of about 11 nm, about 12 nm, about 13 nm, about 14 nm, about 15 nm, about 16 nm, about 17 nm, about 18 nm, about 19 nm, about 20 nm or about 21 nm.

In certain embodiments, the catalyst composition may have a bimodal pore size distribution, for example wherein a first pore radius is from any of about 3 nm, about 4 nm or about 5 nm to any of about 6 nm, about 7 nm, about 8 nm or about 9 nm; and wherein a second pore radius is from any of about 10 nm, about 11 nm, about 12 nm, about 13 nm, about 14 nm or about 15 nm to any of about 16 nm, about 17 nm about 18 nm about 19 nm, about 20 nm or about 21 nm. Pore radius may be determined by ASTM D4641-17.

Present catalyst compositions may have a surface area of from any of about 50 m$^2$/g, about 60 m$^2$/g, about 70 m$^2$/g, about 80 m$^2$/g, about 90 m$^2$/g or about 100 m$^2$/g to any of about 110 m$^2$/g, about 120 m$^2$/g, about 130 m$^2$/g, about 140 m$^2$/g, about 150 m$^2$/g, about 160 m$^2$/g or about 170 m$^2$/g. Surface area may be defined as Brunauer-Emmett-Teller (BET) specific surface area. BET specific surface may be determined by ASTM D3663.

In some embodiments, the shaped form may have a density of from any of about 1.0 g/cm$^3$, about 1.5 g/cm$^3$, about 2.0 g/cm$^3$, about 2.5 g/cm$^3$ or about 3.0 g/cm$^3$ to any of about 3.5 g/cm$^3$, about 4.0 g/cm$^3$, about 4.5 g/cm$^3$ or about 5.0 g/cm$^3$.

In one or more embodiments, the catalyst composition may include one or more binders (e.g., silica, alumina, silica/alumina or clays). In another embodiment, the catalyst composition may include one or more stabilizers (e.g., zirconia). In other embodiments, the catalyst composition may be substantially free of binders or stabilizers. As used herein, "substantially free" or "substantially no" may mean "not purposefully added", for instance ≤5%, ≤4%, ≤3%, ≤2%, ≤1%, ≤0.5%, or ≤0.25%, by weight of such materials may be present.

In one embodiment, an organic compound may be present in the catalyst composition. In some embodiments, an organic compound may be present in the catalyst composition from any of about 0.5 wt %, about 1.0 wt %, about 1.5 wt %, about 2.0 wt %, about 2.5 wt % or about 3.0 wt % to any of about 3.5 wt %, about 4.0 wt %, about 4.5 wt % or about 5.0 wt %. In another embodiment, the organic compound is present in the catalyst formulation no more than about 2.0 wt %. In one embodiment, the organic compound may be selected from a group consisting of cellulose, cellulose gel, microcrystalline cellulose, methyl cellulose, flours, starches (e.g., potato starch), modified starches, graphite, polymers, carbonates, bicarbonates, microcrystalline wax, organic metal salts, palmitic acid, stearic acid, sugar alcohols (e.g., sorbitol) and mixtures thereof. In another embodiment, an organic compound may be selected from a group consisting of Mg palmitate, Mg stearate and mixtures thereof. An organic compound may serve as an extrusion aid in a method of preparation.

Embodiments of the invention also include a method to prepare a catalyst composition, the method comprising preparing a mixture comprising i) MgO and/or Mg(OH)$_2$, ii) alumina and iii) oxides and/or hydroxides of one or more further alkaline earth metals; shaping the mixture into a shaped form; drying the shaped form; and calcining the dried, shaped form. In some embodiments, drying may be performed prior to a shaping step. The shaped form is this case then may or may not be further subjected to a drying step. In some embodiments, the method comprises adding an organic compound to the mixture.

Embodiments of the invention include a method of isomerizing an olefin, the method comprising contacting the olefin with the catalyst composition as described herein. Olefins include butene, pentene and hexene. "Olefin isomerization" may mean an unsaturated bond of an olefin will undergo a shift from one carbon-carbon location to another, for instance from a 1-position to a 2-position, for example isomerization of 1-hexene to 2-hexene.

A certain embodiment includes a method of isomerizing 1-butene to 2-butene, the method comprising contacting 1-butene with a catalyst composition comprising MgO, Al$_2$O$_3$ and one or more further alkaline earth metal oxides.

Another embodiment includes a method of olefin isomerization, the method comprising contacting 1-butene, 1-pentene or a mixture thereof with the catalyst composition described herein to provide 2-butene, 2-pentene or a mixture thereof.

Embodiments of the invention include a method of preparing propylene, the method comprising contacting a feed stream containing 1-butene with ethylene in the presence of a catalyst composition comprising MgO, Al$_2$O$_3$ and one or more further alkaline earth metal oxides and a metathesis catalyst.

Another embodiment incudes a method of preparing propylene, the method comprising contacting a feed stream containing 1-butene, 1-pentene or a mixture thereof with ethylene in the presence of the catalyst composition described herein and a metathesis catalyst.

The articles "a" and "an" herein refer to one or to more than one (e.g. at least one) of the grammatical object. Any ranges cited herein are inclusive. The term "about" used throughout is used to describe and account for small fluctuations. For instance, "about" may mean the numeric value may be modified by ±5%, ±4%, ±3%, ±2%, ±1%, ±0.5%, ±0.4%, ±0.3%, ±0.2%, ±0.1% or ±0.05%. All numeric values are modified by the term "about" whether or not explicitly indicated. Numeric values modified by the term "about" include the specific identified value. For example "about 5.0" includes 5.0.

U.S. patents, U.S. patent applications and published U.S. patent applicants discussed herein are hereby incorporated by reference.

Unless otherwise indicated, all parts and percentages are by weight. Weight percent (wt %), if not otherwise indicated, is based on an entire composition free of any volatiles, that is, based on dry solids content.

Examples

Catalyst compositions are prepared as follows. Aluminum hydroxide is peptized with nitric acid with a liquid to solids weight level of from about 0.5 to about 0.8. Hydrated magnesium oxide/hydroxide is ground to a particle size of less than about 250 microns and added to the alumina mixture. A further alkali metal hydroxide is added. The resulting mixture is mixed in a torque rheometer and extruded through a 3 mm opening. The cylindrical 3 mm extrudates are cut into 5 mm to 15 mm sections and are dried at 120° C. for 16 hours. The cylinders are calcined at 550° C. for 2 hours. The calcined cylinders are allowed to cool and are further cut into 2 mm to 10 mm sections.

The following catalyst compositions are prepared and properties reported. Metals are in weight percent oxides of Mg, Al and further alkaline earth (AE), based on the total composition. The alkaline earth is Ca in samples 3-5 and 12-17; is Sr in sample 10 and is Ba in sample 11. Sample 1 is in a form of tablets. All others are extruded cylinders. Crush strength is reported in lbs/mm. Surface area is reported in m$^2$/g. Pore volume is reported in cm$^3$/g.

| sample | Ma/Al/AE | crush strength | surface area | pore volume |
|---|---|---|---|---|
| 1 | 100/0/0 | — | 193 | 0.34 |
| 2 | 0/100/0 | 15 | 189 | 0.74 |
| 3 | 0/0/100 | 9.5 | 8 | 0.03 |
| 4 | 67/0/33 | 9.7 | 17 | 0.06 |
| 5 | 0/40/60 | 6.6 | 17 | 0.09 |
| 6 | 50/50/0 | 2.6 | 120 | 0.48 |
| 7 | 67/33/0 | 1.5 | 135 | 0.67 |
| 8 | 60/40/0 | 2.0 | 145 | 0.65 |
| 9 | 20/80/0 | 3.4 | 245 | 0.69 |
| 10 | 56/40/4 | 3.4 | 118 | 0.57 |
| 11 | 50/40/10 | 2.1 | 113 | 0.50 |
| 12 | 70/15/15 | 4.2 | 41 | 0.27 |
| 13 | 40/30/30 | 4.3 | 29 | 0.17 |
| 14 | 44/17/39 | 9.2 | 101 | 0.49 |
| 15 | 44/40/16 | 5.3 | 130 | 0.61 |
| 16 | 56/40/4 | 2.0 | 160 | 0.61 |
| 17 | 50/40/10 | 3.9 | 113 | 0.58 |

The samples are tested for conversion of 1-butene to propylene in the presence of ethylene and a metathesis catalyst. A stainless steel tube reactor entrance (top bed) contains 3 g of one of samples 1-17. The reactant exit (bottom bed) contains a mixture of 9 g of one of samples 1-17 and 3 g of a metathesis catalyst comprising WO3 on silica.

The weight hourly space velocity (WHSV) is 26.66 based on the metathesis catalyst and 6.67 based on samples 1-17. Conditions: temperature=300° C.; pressure=400 psi; ethylene/1-butene feed ratio=1.8; 250-355 micron silicon carbide packed in voids. Performance of samples 1-17 for propylene productivity, propylene selectivity and 2-butene/1-butene isomerization ratio are found below.

| sample | propylene productivity | propylene selectivity | 2-butene/ 1-butene ratio |
|---|---|---|---|
| 1 | 24.5 | 95.1 | 2.31 |
| 2 | 12.0 | 88.0 | 0.52 |
| 3 | 15.2 | 88.0 | 0.60 |
| 4 | 17.2 | 90.6 | 0.67 |
| 5 | 16.0 | 90.6 | 0.73 |
| 6 | 24.5 | 94.5 | 2.65 |
| 7 | 24.0 | 94.6 | 2.79 |
| 8 | 24.0 | 94.7 | 2.72 |
| 9 | 12.4 | 93.4 | 0.80 |
| 10 | 25.1 | 95.7 | 3.00 |
| 11 | 23.5 | 94.5 | 2.87 |
| 12 | 21.0 | 93.0 | 1.58 |
| 13 | 18.5 | 91.0 | 1.01 |
| 14 | 23.9 | 95.1 | 2.42 |
| 15 | 24.3 | 95.2 | 2.55 |
| 16 | 26.5 | 96.0 | 3.10 |
| 17 | 27.0 | 96.3 | 3.00 |

The invention claimed is:

1. A catalyst composition comprising MgO from about 44 wt % to about 67 wt %, $Al_2O_3$ from about 30 wt % to about 50 wt %, and one or more further alkaline earth metal oxides, wherein wt % is calculated based on the total weight of the catalyst composition, wherein the catalyst composition is in a shaped form, and wherein the catalyst composition has a pore volume of about 0.3 $cm^3$/g to about 0.72 $cm^3$/g as determined according to ASTM D4284.

2. The catalyst composition according to claim 1, wherein the shaped form is selected from a group consisting of agglomerates, tablets, rings, stars, wagon wheels, extrudates, rods, cylinders, spheres, spheroids, briquettes and pellets.

3. The catalyst composition according to claim 1, having an average largest diameter from about 1 mm to about 25 mm.

4. The catalyst composition according to claim 1, wherein the shaped form is cylinder-like with an average diameter of from about 1 mm to about 8 mm and an average length of from about 2 mm to about 20 mm.

5. The catalyst composition according to claim 1, wherein the shaped form is star-like.

6. The catalyst composition according to claim 1, further comprising one or more metal hydroxides selected from the group consisting of $Mg(OH)_2$, $Al(OH)_3$, and hydroxides of one or more further alkaline earth metals.

7. The catalyst composition according to claim 1, wherein the catalyst composition is in a form of an extrudate.

8. The catalyst composition according to claim 1, further comprising one or more alkaline earth metal oxides selected from CaO, SrO and BaO.

9. The catalyst composition according to claim 1, further comprising CaO.

10. The catalyst composition according to claim 1, comprising from about 3 wt % to about 20 wt % of the one or more further alkaline earth metal oxides, in total, based on the total weight of the composition.

11. The composition according to claim 1, wherein the composition has one or more of:
    a crush strength of ≥2.0 lbs/mm,
    or
    a surface area of from about 50 $m^2$/g to about 170 $m^2$/g.

12. A method to prepare the catalyst composition of claim 1, the method comprising:
    preparing a mixture comprising i) MgO and/or $Mg(OH)_2$, ii) alumina and iii) oxides and/or hydroxides of one or more further alkaline earth metals;
    shaping the mixture into a shaped form;
    drying the shaped form; and
    calcining the dried, shaped form.

13. A method of preparing propylene, the method comprising contacting a feed stream containing 1-butene, 1-pentene or a mixture thereof with ethylene in the presence of the catalyst composition according to claim 1 and a metathesis catalyst.

14. A method of isomerizing an olefin, the method comprising contacting the olefin with the catalyst composition according to claim 1.

15. A method of olefin isomerization, the method comprising contacting 1-butene, 1-pentene or a mixture thereof with the catalyst composition of claim 1 to provide 2-butene, 2-pentene or a mixture thereof.

* * * * *